United States Patent
Schaffler et al.

(10) Patent No.: US 7,241,418 B2
(45) Date of Patent: Jul. 10, 2007

(54) METHOD FOR IMMOBILIZING CONJUGATES IN DIAGNOSTIC TESTS

(75) Inventors: Jurgen Schaffler, Weinheim (DE); Barbara Upheimer, Iffeldorf (DE)

(73) Assignee: Roche Diagnostics Corporation, Indianapolis, IN (US)

(*) Notice: Subject to any disclaimer, the term of this patent is extended or adjusted under 35 U.S.C. 154(b) by 214 days.

(21) Appl. No.: 11/174,227

(22) Filed: Jul. 1, 2005

(65) Prior Publication Data

US 2006/0003390 A1 Jan. 5, 2006

Related U.S. Application Data

(62) Division of application No. 09/795,654, filed on Feb. 28, 2001, now Pat. No. 6,998,246.

(30) Foreign Application Priority Data

Feb. 29, 2000 (DE) ................ 100 09 503

(51) Int. Cl.
*B01L 3/00* (2006.01)
(52) U.S. Cl. ............ 422/61; 422/56; 422/58; 435/4; 435/7.5; 435/7.94; 435/287.7; 435/287.8; 435/810; 436/514; 436/518; 436/807; 436/808
(58) Field of Classification Search .......... 422/61, 422/56, 58; 436/514, 518, 807, 808; 435/4, 435/7.5, 7.94, 810, 287.7, 287.8
See application file for complete search history.

(56) References Cited

U.S. PATENT DOCUMENTS

| 4,434,227 A | 2/1984 | Unger |
|---|---|---|
| 4,806,311 A | 2/1989 | Greenquist |
| 4,859,612 A | 8/1989 | Cole et al. |
| 5,028,535 A | 7/1991 | Buechler et al. |
| 5,141,850 A | 8/1992 | Cole et al. |
| 5,212,063 A | 5/1993 | Ofenloch-Hahnle et al. |
| 5,451,504 A | 9/1995 | Fitzpatrick et al. |
| 5,512,659 A | 4/1996 | Ullman et al. |
| 5,661,019 A | 8/1997 | Oh et al. |
| 5,874,216 A | 2/1999 | Mapes |
| 6,046,058 A | 4/2000 | Sun |
| 6,121,008 A | 9/2000 | Fitzpatrick et al. |
| 6,133,048 A | 10/2000 | Penfold et al. |
| 6,376,195 B1 | 4/2002 | Mapes |
| 6,489,129 B1 | 12/2002 | Faatz et al. |
| 6,815,217 B2 | 11/2004 | Karl et al. |

FOREIGN PATENT DOCUMENTS

| EP | 0 291 194 A1 | 4/1988 |
|---|---|---|
| EP | 0 833 157 A1 | 4/1998 |
| EP | 0 842 949 A1 | 5/1998 |
| WO | WO 96/38720 | 12/1996 |
| WO | WO 00/31538 | 6/2000 |

*Primary Examiner*—Bao-Thuy L. Nguyen
(74) *Attorney, Agent, or Firm*—McDonnell Boehnen Hulbert & Berghoff LLP

(57) ABSTRACT

The invention concerns a method for the detection of an analyte in a sample using analyte-specific conjugates which have at least one heterologous group for an analyte-independent binding to a control zone. The present invention additionally provides new conjugates and reagent kits.

14 Claims, 4 Drawing Sheets

D-DIMER TEST STRIP CONTAINING A DIGOXIGENIN-LABELLED ANTIBODY-GOLD CONJUGATE SIGNAL LINE 150 mM HEPES BUFFER CONTAINING D-DIMER CALIBRATOR

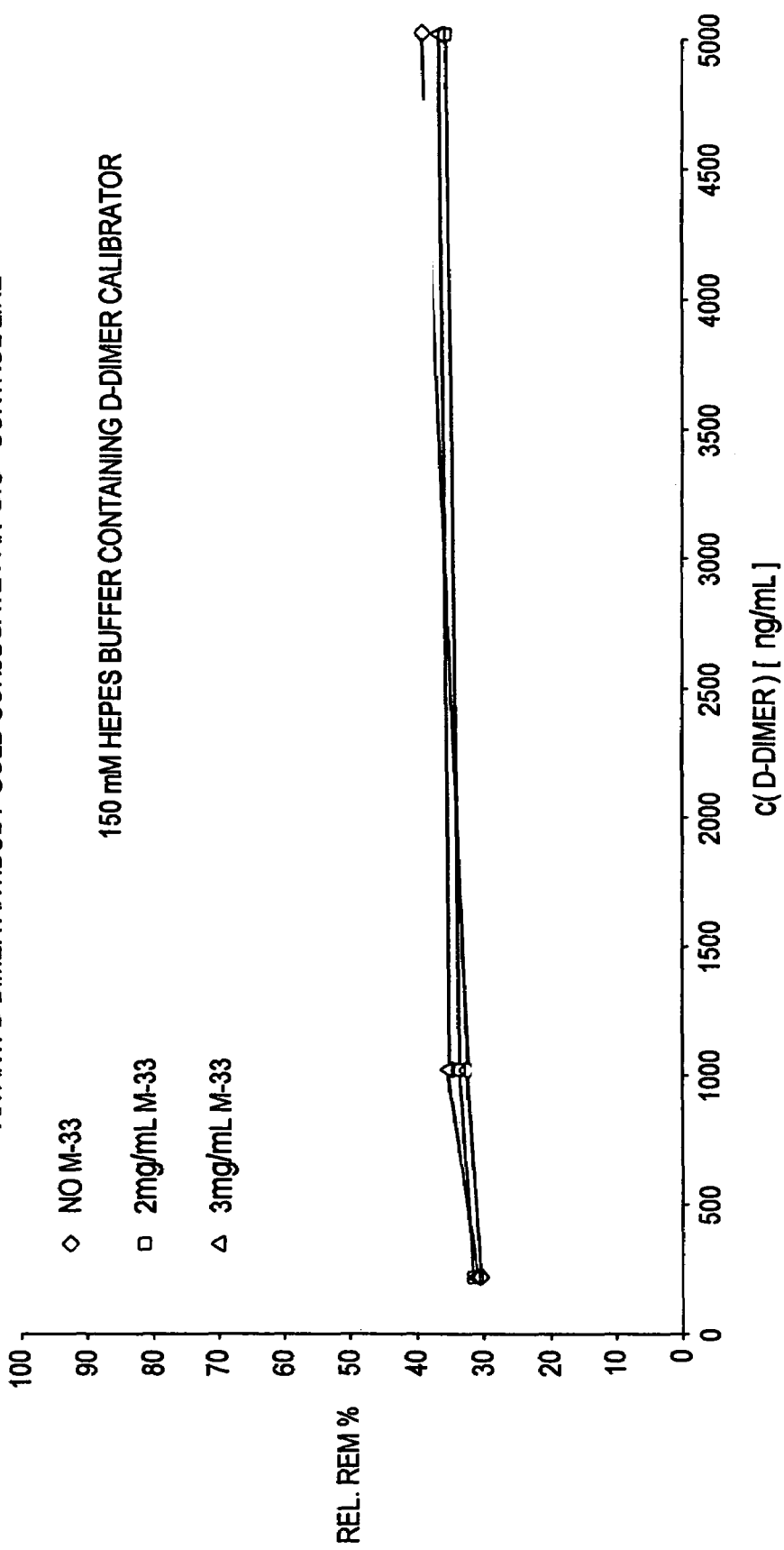

METHOD FOR IMMOBILIZING CONJUGATES IN DIAGNOSTIC TESTS

CROSS REFERENCE TO RELATED APPLICATION

This application is a divisional application of U.S. application Ser. No. 09/795,654, filed Feb. 28, 2001, now U.S. Pat. No. 6,998,246 which claims priority to German Patent Application No. 100 09 503.8 filed Apr. 19, 2001.

BACKGROUND OF THE INVENTION

1. Field of the Invention

The invention concerns a method for detecting an analyte in a sample using analyte-specific conjugates which have at least one heterologous group for an analyte-independent binding to a control zone. The present invention additionally provides new conjugates and reagent kits.

2. Description of the Related Art

Analyte-specific reagents such as specific binding partners for the analyte to be determined or/and analyte analogues are used to detect analytes, e.g. substances of diagnostic relevance, in a sample. In heterogeneous detection methods a solid phase is used to bind the analyte such that the analyte can be separated from other components in order to carry out a qualitative or quantitative test. This solid phase binding can be mediated by an additional analyte-specific receptor which is bound to the solid phase before or during the test procedure. In a detection method based on the principle of a sandwich test a specific binding partner for the analyte can be bound to the solid phase and the analyte is detected by means of a free binding partner that is specific for the analyte and carries a labelling group. In a competitive detection method a specific binding partner for the analyte can also be used as the solid phase analyte-specific reagent and the analyte is detected indirectly by binding a free labelled analyte analogue to the solid phase.

Test strips are a special technical embodiment of heterogeneous detection methods which contain a defined analyte detection zone for the quantitative or qualitative detection of the analyte. The free analyte-specific receptor used for the detection preferably carries a direct label i.e. a group which directly generates a signal which enables a visual qualitative evaluation of the test as well as an instrument-based quantitative determination.

In addition to the analyte detection zone, diagnostic test strips also contain a control zone which allows the user to differentiate between a negative test result and an incorrect use or functional defect of the test. This control zone is usually designed such that it enables the free analyte-specific receptor to be immobilized independently of the presence of the analyte in the sample. Hence this control zone in any case becomes coloured when the test functions correctly.

The binding of the free analyte-specific receptor in the control zone can be achieved by various methods. If the free analyte-specific receptor is a specific binding partner for the analyte, then the analyte, an analyte analogue or an epitope of the analyte can be immobilized in the control zone which captures the free analyte binding partner. If the free binding partner is an antibody, an antibody, antigen analogue or an epitope of the antigen that reacts with the antibody can therefore be used for the control zone.

However, this embodiment of the control zone cannot be realised in some cases because the analyte is not available in adequate amounts or/and is not sufficiently characterized in order to prepare analogues or/and epitopes thereof or/and the specific binding partner recognizes regions of the analyte that cannot be transformed into an epitope or which are no longer accessible after immobilization on the test strip.

In such cases a receptor directed against a homologous non-analyte binding region of the binding partner has been previously used in order to capture the free analyte-specific binding partner in the control zone of the test strip. If the binding partner is an antibody, anti-antibodies which recognize the constant region of the detection antibody or other reagents that can specifically bind to immunoglobulins such as protein A or protein G have been used as control receptors.

A signal generating reaction in the control zone is important in order to make a valid interpretation of the result of a heterogeneous detection method in a test strip format since it is only possible in this manner to check the correct function of the test strip. A coloration of only the control region should be interpreted as a negative result of a functional test-whereas an additional coloration of the analyte detection zone represents a positive test result which usually means detection of the presence of an analyte in the tested sample.

However, the binding event which ensures the coloration of the control zone may be impaired for various reasons. For example the capacity of the free analyte binding partner may be substantially exhausted by high analyte concentrations in the sample and thus it cannot or can no longer adequately bind to an analyte or epitope or analogue thereof immobilized in the control zone. The control zone then only colours weakly or not at all (Hook effect).

If other receptors that are independent of the analyte recognition of the binding partner such as antibody-binding substances, especially anti-antibodies, are used as capture reagents in the control region of the test strip, this reduces the risk of a loss of function by the Hook effect. However, this concept of test strip control has other serious disadvantages. Thus in many cases biological materials such as blood, plasma or serum are used as samples. A person skilled in the art knows that these materials contain substances that can bind antibodies which can cause interferences in an immunological test that uses antibodies as specific capture and detection reagents resulting in false-positive or false-negative results. In order to prevent such erroneous measurements, unspecific immunoglobulins of that animal species from which the specific detection antibodies were derived are usually added as components to eliminate interference. The amount of these interference-eliminating antibodies exceeds the amount of analyte-specific antibodies by several fold. They are capable of binding to the capture reagents of the control region of the test strip which are directed against the detection antibody and thus compete with the detection reagent for binding sites. Consequently smaller-amounts of the detection reagent are immobilized, the coloration of the control zone is much weaker or it does not occur at all.

SUMMARY OF THE INVENTION

The object of the present invention was to provide heterogeneous detection methods in which control zones are used which do not have the aforementioned disadvantages of the prior art.

This object is achieved by using derivatized free analyte-specific receptors i.e. one or several heterologous structural elements are introduced which were not previously present in the free receptor and which are independent of its label and its property to specifically bind the analyte or an analyte binding partner. As a result of the newly introduced structural element the derivatized receptor can be recognized and bound by a receptor which is directed against it. This additional receptor is immobilized in the control zone of the solid phase used for a heterogeneous test and thus it is possible to capture the labelled free receptor in this zone. The capture reaction is not influenced by the amount of analyte in the sample. The heterologous structural element which enables receptor binding can be selected such that other reactions that interfere with the receptor binding are substantially reduced e.g. by interference-eliminating substances.

Hence a first aspect of the present invention concerns a method for the detection of an analyte in a sample comprising the steps (a) preparing a solid phase comprising an analyte detection zone and a control zone in which the analyte detection zone is used to quantitatively or/and qualitatively detect the analyte in the sample and the control zone is used to test the functional capability of the test reagent, (b) contacting the solid phase with the sample and the test reagent, the test reagent containing a free analyte-specific receptor and at least one heterologous structural element for a specific binding to the control zone and the heterologous structural element being independent of the analyte-specific properties of the receptor, and (c) determining the presence or/and the amount of analyte in the sample by means of the analyte detection zone and checking the test function by means of the control zone.

BRIEF DESCRIPTION OF THE DRAWINGS

FIG. 4 shows the effect of the presence of a monoclonal interference-elimination antibody on the development of an anti-digoxigenin antibody control line on a D-dimer test strip.

DETAILED DESCRIPTION OF THE INVENTION

Figure 1:
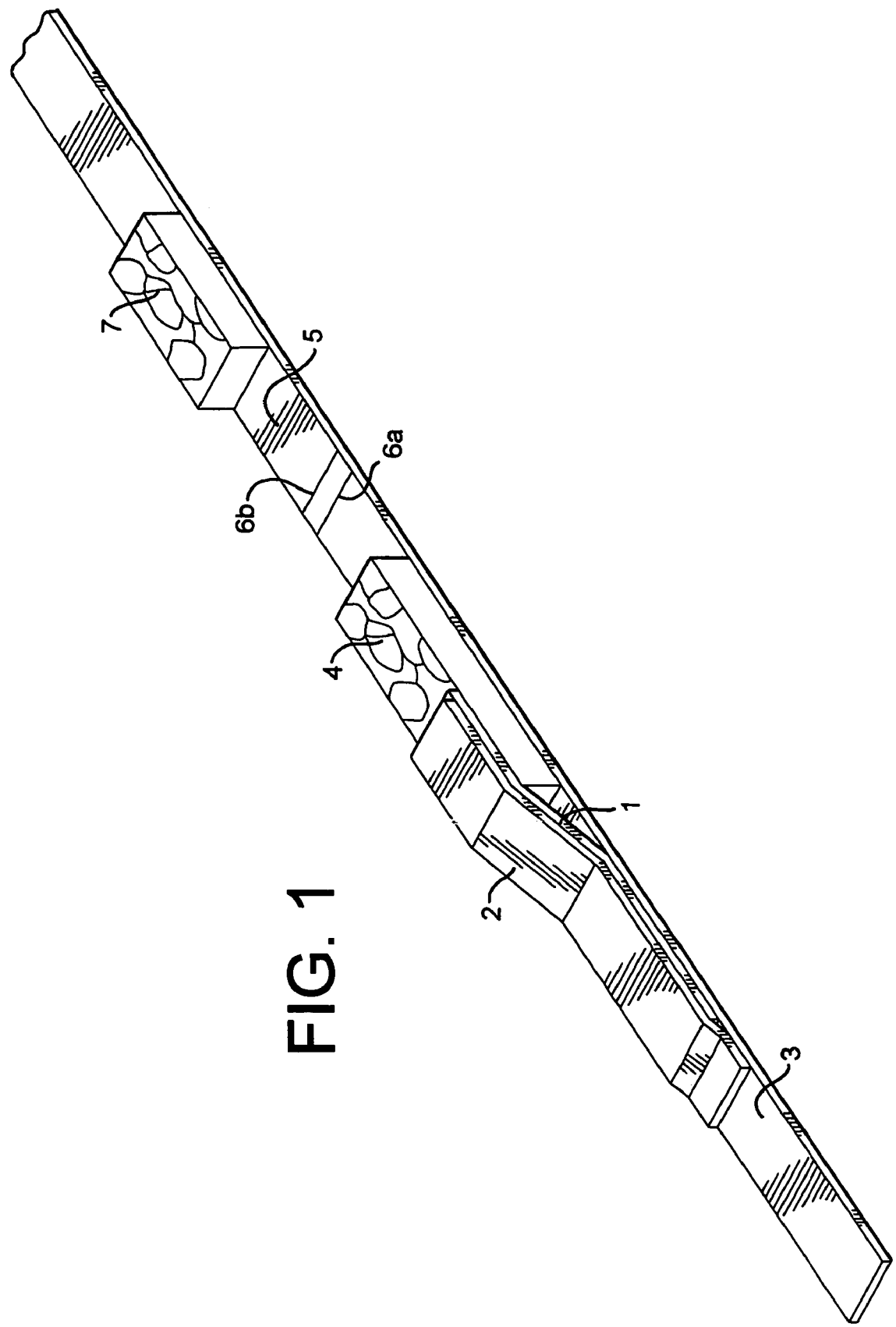
FIG. 1 is a diagram depicting a test strip in accordance with a preferred embodiment of the invention. The test strip contains a waterproof carrier foil (3) on which the following are mounted: a carrier fleece containing a labeled reagent (1) and a carrier fleece containing an immobilizable reagent (2) as well as a fleece (4) for separating solid sample components such as red blood cells. In addition, a carrier membrane with a signal zone (6a) and a control zone (6b) is also mounted on the carrier foil (1). Finally the carrier contains an absorbent fleece (7). The carrier fleeces (2, 1, 4, 5, and 7) are arranged such that they are in chromatographic contact with one another. A sample applied to the fleece (2) flows over (1), (4), and (5) into the absorbent fleece (7).

The method according to the invention is particularly suitable for solid phases which comprise a porous material such as absorbent test strips. Furthermore the method according to the invention is also suitable for other types of solid phases e.g. non-porous support materials in the form of array arrangements which have spatially defined control zones in addition to one or several analyte binding zones.

The analyte detection zone of the solid phase is preferably designed such that an analyte-specific receptor, e.g. an antibody or antibody fragment that can bind specifically to the analyte, is immobilized on it. The immobilization can take place before or during the test procedure preferably by means of high affinity interactions such as streptavidin or avidin/biotin. On the other hand, the immobilization can also be achieved adsorptively or by covalent binding.

In a test procedure according to the sandwich principle the binding of the analyte to the solid phase is detected by using a free receptor which comprises a specific binding partner for the analyte e.g. another antibody-directed against the analyte. In a competitive test procedure it is possible to use an analyte analogue as the free receptor. The free receptor is preferably directly or indirectly labelled. In the case of a direct label the free receptor carries a signal-generating group and in the case of an indirect label it carries a group that can bind to a signal-generating group. Examples of signal-generating groups are radioactive labels, enzymes, fluorescent or luminescent groups or coloured labels. Direct labels are particularly preferred and especially groups that can be detected by optical methods such as gold or other metal particles, coloured or fluorescent particles e.g. latex particles or silicate particles etc.

In contrast to the known methods, a free receptor is used according to the present invention which is bound to at least one heterologous structural element which serves to bind it to a control zone. A heterologous structural element in the sense of the present invention is understood as a structural element which is associated with the receptor in a non-natural manner. The heterologous structural element can be directly bound to the receptor. The binding between the heterologous structural element can, however, also be indirectly mediated e.g. by means of a carrier.

The heterologous structural element is different from the analyte-specific binding group of the free receptor and also different from the labelling group of the free receptor if one is present. Examples of suitable heterologous structural elements are proteins, peptides, carbohydrates, nucleic acids, nucleic acid analogues, high and low molecular natural or synthetic haptens and all molecules for which a specific receptor exists or can be generated. The heterologous structural element is preferably a low molecular (MW≦3000) hapten, a peptide with up to 25 amino acids or biotin. The heterologous structural element can be bound covalently or by non-covalent interactions to the free receptor. A covalent binding is preferred.

The heterologous structural element can for example be a group that is attached to the free receptor by a chemical derivatization reaction e.g. a hapten coupled to a polypeptide or a nucleic acid. This derivatization reaction can occur before or after the introduction of the labelling groups. For the derivatization reaction the heterologous structural element is usually contacted with the free receptor in the form of an activated derivative e.g. as an active ester such as an N-hydroxy-succinimide ester or as a maleimide in which case it is bound to free amino or thiol groups of the receptor.

On the other hand the heterologous structural element can also be a recombinant peptide, polypeptide or nucleotide sequence which is attached to a receptor of a peptide, polypeptide or nucleic acid type.

The free receptor can be selected from peptides, polypeptides, glycoproteins, lipoproteins, nucleic acids, nucleic acid analogues, saccharides, polysaccharides and other biological substances and it is preferably a peptide or polypeptide for example an antibody. Such an antibody can for example be derivatized with a hapten e.g. digoxigenin or fluorescein and subsequently be adsorptively coupled to a labelling group e.g. colloidal metal particles such as gold particles. Such a doubly-modified antibody is then used in combination with a control zone which contains immobilized anti-digoxigenin antibodies.

In a further embodiment of the method according to the invention the binding of the heterologous structural element to the free receptor can be mediated by a carrier, preferably by coimmobilization, i.e. sequential or/and simultaneous immobilization, on a particle e.g. by adsorption. The particles are preferably selected from the above-mentioned direct labels e.g. metal, dye or fluorescent particles. In the course of the production process it is possible to bind not only the free receptor to these particles but also additional accompanying substances such as stabilizers like bovine serum albumin, unspecific antibodies (e.g. IgG) or wetting agents. According to the present invention, the heterologous structural element can now be introduced into one of these accompanying substances to form a conjugate which comprises the free receptor and the heterologous structural element in the form of two different molecules that are coimmobilized on a particle. This conjugate fulfils the function of a labelled free receptor and can, on the other hand, be captured by a binding partner directed against the structural element.

The method according to the invention can be used to detect diagnostic relevant analytes in biological samples. Examples of biological samples are body fluids such as blood, serum, plasma, urine, saliva and sperm, tissue samples, samples from cell cultures etc. The sample to be tested is contacted with the test reagent and the solid phase under suitable conditions whereby the order in which the individual components are contacted is generally not critical. When test strips are used, the test reagent is generally present in a dry form on the test strip and is dissolved by contact with the liquid sample. The capillary action of the absorbent test strip material causes the liquid to then subsequently migrate to the analyte detection zone and control zone where the test result can then be read.

The method according to the invention is basically suitable for all types of detection systems of the X/anti-X type in which an analyte X can be detected due to a high affinity specific interaction with a receptor anti-X that can bind the analyte. The method is preferably an immunological detection method or a nucleic acid hybridization method. However, other detection methods such as sugar/lectin detection methods are of course also suitable.

The use of free analyte-specific receptors which additionally carry a heterologous structural element for binding to a control zone is particularly suitable for detection methods in which reagents that eliminate interference have to be present to exclude the frequent occurrence of false results. Examples of such interference-eliminating reagents are substances that are structurally related to the free receptor but are not analyte-specific e.g. antibodies from the same species or/and from the same immunoglobulin class. It is just in such cases that the present invention may be the only possibility of providing a functional control zone.

Yet a further subject matter of the present invention is a reagent kit which is especially suitable for use in a method according to the invention. The reagent kit according to the invention for the detection of an analyte in a sample contains:

(a) a solid phase comprising an analyte detection zone and a control zone in which the analyte detection zone is used to quantitatively or/and qualitatively detect the analyte in the sample and the control zone is used to check the function of the test reagent and (b) a test reagent comprising a free analyte-specific receptor and at least one heterologous structural element for a specific binding to the control zone, the heterologous structural element being independent of the analyte-specific properties of the receptor.

The free receptor preferably carries a signal-generating group or a group that can bind to a signal-generating a group, the free receptor particularly preferably carries a directly detectable signal-generating group. The reaction kit according to the invention preferably additionally contains an analyte-specific solid phase receptor which can be present on the analyte detection zone in an immobilized form or which contains a solid phase binding group that can be immobilized on the analyte detection zone for example by means of a high affinity interaction such as streptavidin/biotin. The solid phase contained in the reagent kit is preferably a porous material, in particular an absorbent test strip. The reagent kit can also contain substances that eliminate interference and are structurally similar to the free receptor.

Yet a further aspect of the present invention is a conjugate containing:
(a) at least one first specific binding group which can interact with high affinity with a first binding partner,
(b) at least one labelling group in particular a directly detectable signal-generating group and
(c) at least one second specific binding group comprising a heterologous structural element which is different from the groups (a) and (b) and can interact with high affinity with a second binding partner.

The conjugate according to the invention is especially suitable as a component of a test reagent in a detection method in particular in an inventive detection method or/and as a component of an inventive reagent kit.

The first specific binding group of the conjugate is preferably an analyte-specific binding group i.e. a group which can undergo a specific high affinity interaction which the analyte itself or with an analyte binding partner. The labelling group is preferably one that can be directly detected by optical methods e.g. a metal particle. The second specific binding group comprises the aforementioned heterologous structural element and is different from the first specific binding group and the labelling group. The second specific binding group allows a high affinity interaction with the second binding partner independent of a binding to the first binding group.

In this conjugate the heterologous structural element can be covalently linked to the first specific binding group as mentioned above. However, the invention also concerns a conjugate in which the first specific binding group and the heterologous structural element are located on two different molecules which are present in a co-immobilized form on a particle.

The present invention is additionally elucidated in more detail by the following figures and examples.

EXAMPLES

Example 1

Derivatization of a Monoclonal Antibody with Activated Digoxigenin 10 mg of a purified monoclonal antibody to D-dimer is dissolved at a concentration of 10 mg/ml in 100 mM potassium phosphate buffer, pH 8.5 and incubated in a water bath to 25° C. 0.065 ml of a solution of digoxigenin-3-O-methylcarbonyl-∈-aminocarboxylic acid-N-hydroxy succinimide ester (Roche Diagnostics GmbH, Mannheim, Germany) in dimethyl-sulfoxide (1.052 mg/ml) is added slowly while stirring. The mixture is incubated for 90 min at 25° C. while stirring. Afterwards lysine hydrochloride is added to the mixture to a final concentration of 10 mM while keeping the pH value at pH 8.5. After a further 15 minute incubation at 25° C. the material is flow-dialysed against a 5000-fold volume of 30 mM potassium phosphate buffer, pH 7.6, 100 mM sodium chloride.

Example 2

Preparation of a Detection Reagent for a Rapid Immunological Test by Immobilizing a Digoxigenin-labelled Monoclonal Antibody on Colloidal Gold 500 ml colloidal gold with an average particle diameter of 20 nm (optical density 1.0 at 520 nm) is incubated at room temperature and filtered through a cellulose nitrate filter with a pore size of 0.2 mm. The pH is adjusted to pH 7.6 by addition of potassium carbonate.

50 ml of a solution of a digoxigenin-labelled antibody to D-dimer (prepared as in example 1) at a concentration of 0.1 mg/ml Tris/HCl buffer (2 mM Tris/HCl, pH 7.6, 20 mM sodium chloride) is added to the filtrate. After incubating for 30 minutes while stirring gently, bovine serum albumin is added to the mixture to a final concentration of 1% (w/v) and it is stirred for a further 30 min. Afterwards the material is concentrated by tangential flow ultrafiltration over membranes with an exclusion size of 30,000 Dalton until the optical density (measured at 520 nm) is 20. The antibody-gold conjugate is stabilized by adding sucrose to a final concentration of 4% (w/v) and sodium azide to a final concentration of 0.095% (w/v).

Example 3

Rapid Immunological Test a) Conjugate Carrier

A mixed fleece composed of a DuPont mixed ester fibre, artificial cell-wool and Kuralon strengthened against wet tearing in a weight ratio of 80:20:20 is used as the porous support for the gold conjugate impregnation. The fleece is prepared analogously to the description in EP-A-0 326 135. The fleece (liquid uptake about 30 µl/cm$^2$) is impregnated with a solution which contains 1 ml of the gold conjugated digoxigenin-labelled antibody solution from example 2 and 4 ml HEPES buffer (130 mM HEPES/sodium hydroxide, pH 7.5) It is subsequently dried and cut to a width of 18 mm.

b) Conjugate Carrier Containing Biotinylated Antibodies

A purified second monoclonal antibody to D-dimer is derivatized with biotin using D-biotinoyl-∈-aminocaproic acid-N-hydroxysuccinimide ester (Roche Molecular Biochemicals) analogously to example 1.

A further mixed fleece as described under 3a) is impregnated with a solution which contains 10 µg/ml of the second antibody conjugated with biotin and 10 mg/ml bovine serum albumin in HEPES buffer (130 mM HEPES/sodium hydroxide, pH 7.5) It is subsequently dried and cut to a width of 20 mm.

c) Test Strip

These reagent fleeces i.e. a gold conjugate fleece (1) and a fleece containing biotinylated antibody (2) are used to construct test strips according to FIG. 1 by sealing them onto a carrier foil (3) made of polystyrene (Melinex) by means of a hot-melt adhesive strip. A glass fibre fleece (4) strengthened with 10 parts by weight Kuralon is used to separate red blood cells. The fleece is prepared analogously to the description in EP-B-0 239 002. The glass fibre fleece typically has an area weight of ca. 180/cm$^2$, a thickness of ca. 1.5 mm and an impregnation uptake of ca. 1,400 ml/m$^2$. The fleece is impregnated with an 80 mM 2-morpholine ethane sulfonic acid buffer pH 5.6 which contains 0.2% by weight bovine serum albumin and 0.1% by weight n-octylglucoside. The dried fleece is cut to a width of ca. 12 mm. A solution which contains 4.5 mg/ml (poly)streptavidin (Roche Molecular Biochemicals) in distilled water is applied to a cellulose nitrate membrane (5) (Sartorius SN 11301, 145 µm thickness, 8 µm pore diameter) by means of needle dosing (cannula diameter 0.16 mm) to generate a signal line (6a), and 5 mg/ml sheep polyclonal antibody against mouse antibody (PAK<mouse>, Roche Molecular Biochemicals) in distilled water or 1 mg/ml sheep polyclonal antibody against digoxigenin (PAK<Dig>, Roche Molecular Biochemicals) in PBS is applied to generate a control line (6b). The solutions are applied such that lines (6a, 6b) are formed with a width of ca. 0.5 mm. The cellulose nitrate membrane is subsequently cut to a width of 15 mm longitudinal to the direction of the line. An absorbent fleece (7) is attached to the opposite end of the membrane. A non-impregnated glass fibre fleece strengthened with 5 parts by weight Kuralon is used as the absorbent fleece. The fleece is prepared analogously to the description in EP-B-0 239 002. The fleece typically has an area weight of 180 g/m$^2$ and a thickness of 1.5 mm. It is cut to a width of 7 mm to incorporate it into the test carrier. The sealed test carrier is subsequently cut into individual test strips of 6 mm width.

d) Measurement

Figure 2:
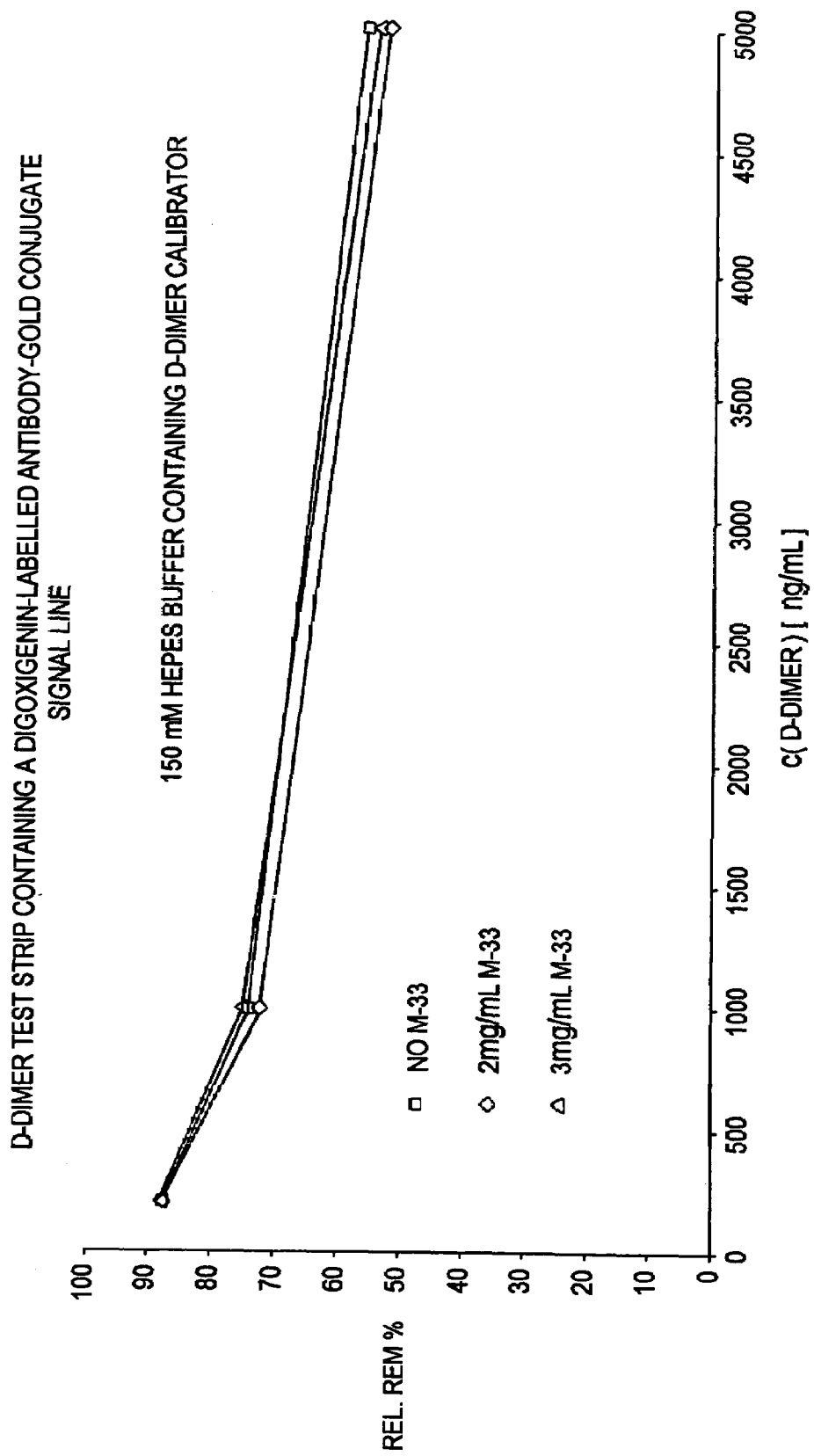
FIG. 2 shows the development of a signal line on a D-dimer test strip containing a digoxigenin labeled antibody-gold conjugate as a test reagent.

The sample (150 µl whole blood, plasma or similar) is applied to the conjugate fleeces which dissolves the conjugates. Analyte present in the sample forms sandwich complexes with the two conjugate antibodies. This solution is transported by capillary forces through the glass fibre fleece where erythrocytes are optionally separated and through the membrane to the absorbent fleece. Biotinylated antibody and sandwich complexes that are formed are captured on the (poly)streptavidin line. A red line of greater or lesser intensity caused by the bound colloidal gold is formed depending on the concentration of the sandwich complex that has formed. Excess gold conjugate is captured on the control line (PAK<mouse> or PAK<Dig>) by binding the monoclonal mouse antibody or the digoxigenin label. The proper function of the test can be observed at this line position by a red colour even when the analyte is absent. After a reaction time of 10 minutes the intensity of the lines is measured with the aid of a CCD camera. FIG. 2 shows the development of the signal line versus the analyte concentration (relative rem %=reflection of the line relative to the uncoloured membrane to the right and left of the line).

Example 4

Test Strip in which Interference has Been Eliminated by HAMA

Increasing amounts of a monoclonal HAMA (human anti-mouse antibody) interference elimination antibody are added to the impregnation formulation in the biotin conjugate fleece according to example 3 to capture anti-mouse antibodies which may be present in the sample to be analysed.

The test strips are prepared as described under example 3.

A series of concentrations of solutions containing analyte is measured as described under example 3.

Figure 3:
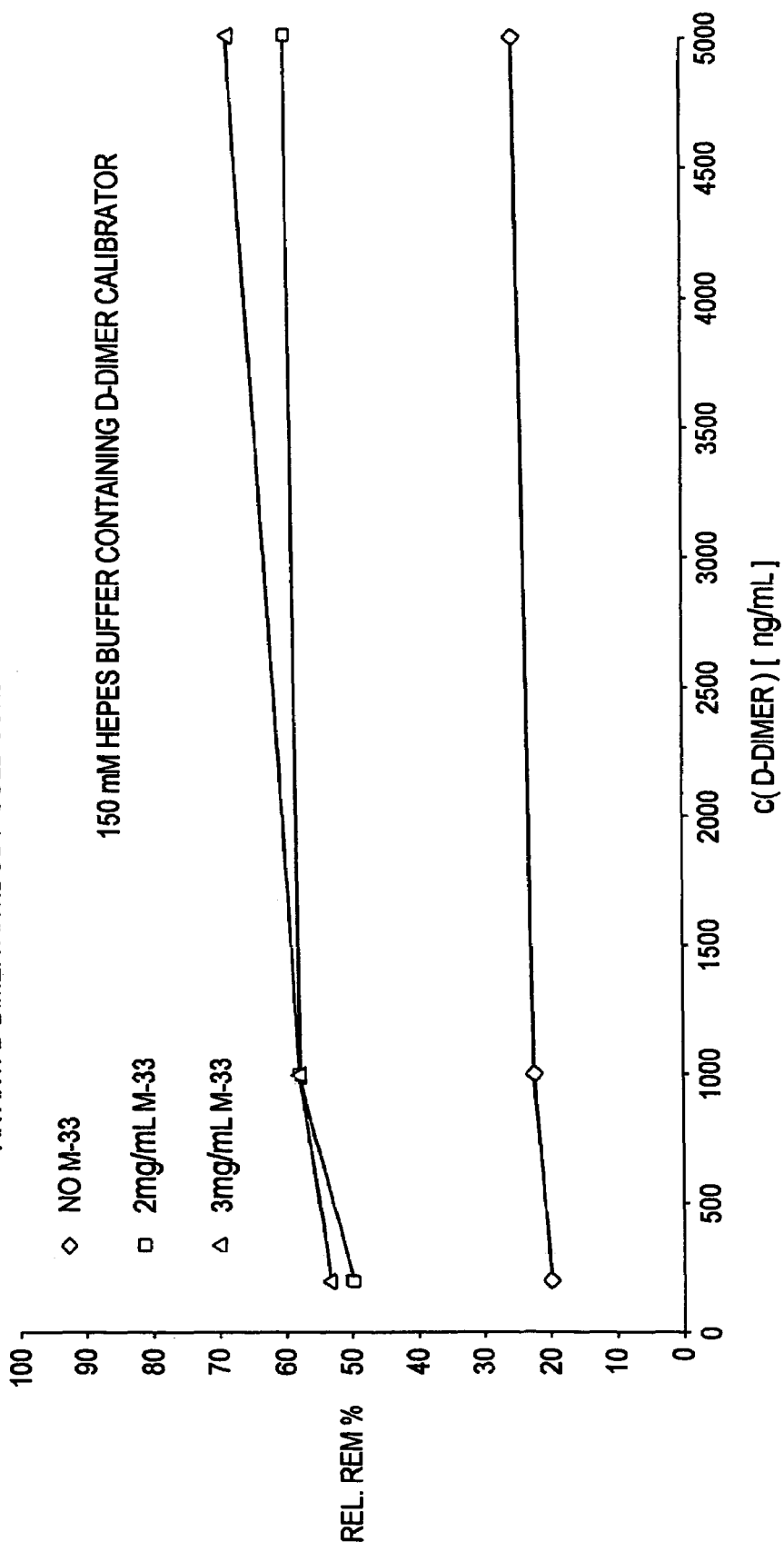
FIG. 3 shows the effect of the presence of a monoclonal interference-elimination antibody on the development of an anti-mouse antibody control line on a D-dimer test strip.

FIG. 3 shows the formation of the control line when using different amounts of interference elimination antibodies when PAK<mouse> is used (rel rem %=reflection of the line relative to the uncoloured membrane to the right and left of the line). The intensity of the line becomes considerably less with increasing amounts of interference elimination antibodies. FIG. 4 shows the formation of the control line when using different amounts of interference elimination antibodies when using PAK<Dig>. The amount of interference elimination antibodies does not have any observable influence on the formation of the control line.

What is claimed is:

1. A kit for the detection of an analyte in a sample, comprising:
   (a) a solid phase comprising an analyte detection zone and a control zone; and
   (b) a test reagent comprising a conjugate comprising an analyte-specific receptor and at least one heterologous structural element coupled to the analyte-specific receptor by covalent binding, wherein the analyte-specific receptor further carries a signal-generating group or a group that can bind to a signal-generating group;
   wherein the analyte detection zone of the solid phase is used to quantitatively or qualitatively detect the analyte in the sample and the control zone of the solid phase is used to test the functional capability of the test reagent; and
   wherein the analyte, if present, binds the analyte-specific receptor and directly or indirectly binds to the analyte detection zone, and the heterologous structural element binds to the control zone.

2. The kit of claim 1, wherein the analyte-specific receptor is immobilized, or is capable of being immobilized, onto the analyte detection zone.

3. The kit of claim 1, wherein the signal-generating group comprises a group that can be detected by optical methods.

4. The kit of claim 3, wherein the signal-generating group is selected from the group consisting of a metal, dye, fluorescent compound, latex particle, and silicate particle.

5. The kit of claim 3, wherein the signal-generating group comprises a gold particle.

6. The kit of claim 1, wherein the solid phase comprises a porous material.

7. The kit of claim 6, wherein the solid phase comprises a fleece.

8. The kit of claim 6, wherein the solid phase is in the form of an absorbent test strip.

9. The kit of claim 1, wherein the heterologous structural element is attached to the analyte-specific receptor by a derivatization reaction.

10. The kit of claim 1, wherein the heterologous structural element is selected from the group consisting of haptens, peptides, and biotin.

11. The kit of claim 10, wherein the heterologous structural element is digoxigenin.

12. The kit of claim 1, wherein the analyte-specific receptor comprises a specific binding partner for the analyte.

13. The kit of claim 1, wherein the analyte-specific receptor is selected from the group consisting of peptides, polypeptides, antibodies, antibody fragments, glycoproteins, lipoproteins, nucleic acids, nucleic acid analogues, saccharides, and polysaccharides.

14. The kit of claim 1, wherein the test reagent further comprises interference elimination substances that are structurally related to the analyte-specific receptor but are not analyte-specific, wherein the interference elimination substances are not attached to the analyte-specific receptor.

* * * * *